United States Patent [19]

Rokugawa et al.

[11] Patent Number: 5,108,934

[45] Date of Patent: * Apr. 28, 1992

[54] QUANTITATIVE IMMUNOASSAY UTILIZING LIPOSOMES

[75] Inventors: Kyuji Rokugawa, Nishinasuno; Masako Hatoh, Yokohama; Yoshio Ishimori, Tokyo, all of Japan

[73] Assignee: Kabushiki Kaisha Toshiba, Kawasaki, Japan

[*] Notice: The portion of the term of this patent subsequent to Apr. 28, 2009 has been disclaimed.

[21] Appl. No.: 157,772

[22] Filed: Feb. 19, 1988

Related U.S. Application Data

[63] Continuation-in-part of Ser. No. 675,607, Nov. 28, 1984, abandoned.

[30] Foreign Application Priority Data

Nov. 30, 1983 [JP] Japan ............................... 58-224509
Feb. 19, 1987 [JP] Japan ............................... 62-34480

[51] Int. Cl.$^5$ ................. G01N 33/536; G01N 33/544; G01N 33/555
[52] U.S. Cl. ..................................... 436/512; 436/519; 436/528; 436/536; 436/826; 436/829
[58] Field of Search ............... 436/829, 528, 519, 536, 436/537, 826, 5

[56] References Cited

FOREIGN PATENT DOCUMENTS 8302069 6/1983 World Int. Prop. O. .......... 436/829

OTHER PUBLICATIONS

Hashimoto et al., "Coating of Liposomes with Subunits ..." *Journal of Immunological Methods* 62 (1983), pp. 155-162.

Primary Examiner—David Saunders
Attorney, Agent, or Firm—Foley & Lardner

[57] ABSTRACT

There is disclosed, in an immunoassay employing an immunoassay reagent comprising liposomes comprised of at least any one of phospholipids and glycolipids, a marker material enclosed in said liposomes, and an antibody or part of the antibody, or an antigen, immobilized on said liposomes by a cross-linking method, the improvement wherein a material for preventing nonspecific lysis of the liposomes is made present together in a reaction mixture.

4 Claims, 8 Drawing Sheets

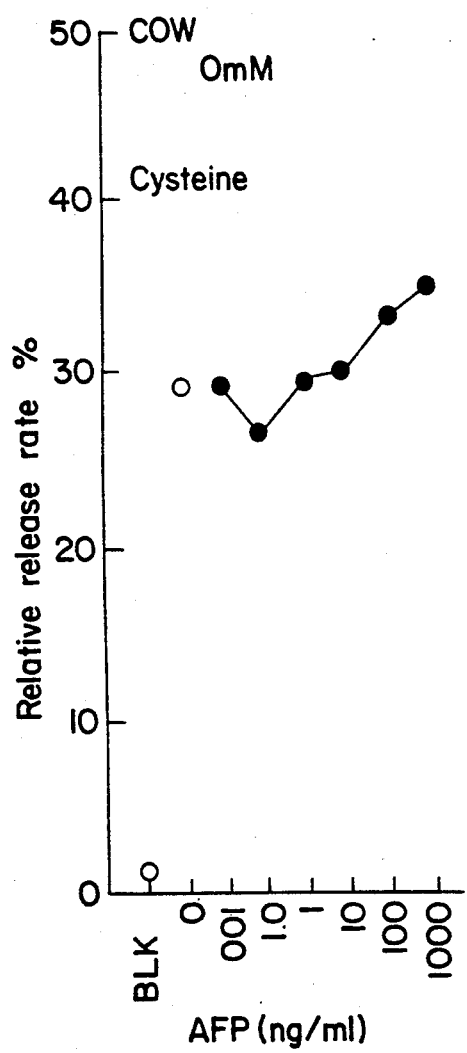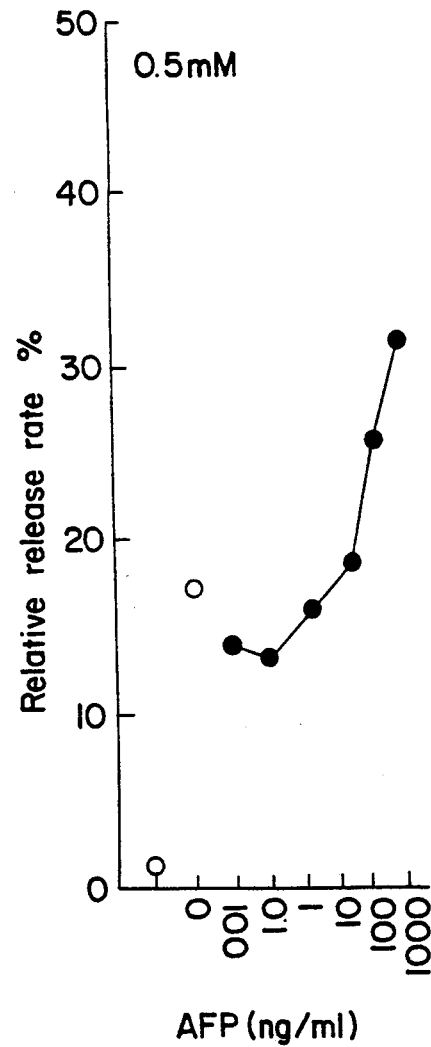
FIG. 11
FIG. 11A

QUANTITATIVE IMMUNOASSAY UTILIZING LIPOSOMES

This is a continuation in part application of our U.S. Ser. No. 675,607 filed Nov. 28, 1984, now abandoned.

BACKGROUND OF THE INVENTION

This invention relates to a reagent for immunoassay and an analytical method using the same, more particularly to a reagent for an immunoassay which is utilized to quantitatively analyze a specific antigen or antibody, an analytical method in which the reagent is employed, and an improvement in an immunoassay for quantitatively analyzing a specific antigen or antibody in a sample.

In recent years, a variety of tumor markers have been found out, as researches on cancers make advances. Typical examples of such tumor markers include α-fetoprotein (AFP), carcinoembryonic antigen (CEA), basic fetoprotein (BFP) and pancreatic oncofetal antigen (POA). Concentrations of these tumor markers in normal human sera are very low (e.g., the concentration of AFP is 10 ng/ml or less). On the other hand, these concentrations of tumor patients are about 10 times as high as the normal human sera in most cases. At any rate, with regard to the quantitative analysis of the tumor markers, a very high detection sensitivity is required.

In order to satisfy this requirement, there has been developed radio immunoassay (RIA) in which an antigen or antibody labelled by a radioactive material is employed. However, the RIA method has been troublesome in points of handling and disposal treatment. For this reason, there has been suggested another immunoassay in which an antigen or antibody labelled with a variety of materials such as enzymes and fluorescent materials in place of the radioactive materials. However, this immunoassay technique also has the drawback that a free antibody and a combined antibody must be separated from each other in any manner. Further, an EMIT method, which has been disclosed in Rosenthal A. F., Vargas M. G. and Klass C. S. (1976), Clin. Chem., Vol. 22, p. 1899, is an epochal method by which measurement can be made in a uniform system without requiring any separation process, but it cannot be fundamentally applied to a protein antigen or antibody having a high molecular weight.

Haxby J. A., Kinsky C. B. and Kinsky S. C. (1968), Biochemistry, Vol. 61, p. 300 has revealed a method by which there is prepared liposomes where a fat-soluble antigen is taken in its membrane and glucose is contained, and glucose discharged from the liposomes due to its breakage caused by an antigen-antibody reaction is quantitatively determined in order to accomplish the quantitative analysis of an antibody. However, if the measurement of the tumor marker is attempted, it will be necessary to support the marker itself or the antibody against this marker, i.e. an immunogloblin which is a kind of protein, on the liposomes. Up to now, the liposomes incorporated into hydrophobic proteins have been feasible, but it has not been reported yet that water-soluble protein-bearing liposomes are contemplated for the aim of immunoassays of antigens or antibodies. This reason is that a technique of supporting the water-soluble protein on liposomes has not been established.

Further, in Japanese Provisional Patent Publication (KOKAI) No. 132564/1981 entitled "Product for immunological analysis and method for preparing the same", there is disclosed a method by which liposomes supporting an antigen or antibody thereon and including an enzyme therein are used to carry out an immunoassay. In this suggested method, a protein is supported on the liposomes by using a bifunctional cross-linking agent such as glutaraldehyde. However, it has been realized from the present inventors' researches that if the antigen is supported on the liposomes with the aid of the cross-linking agent, the activity of the antigen will be generally reduced and the liposomes breakage to be caused by the antigen-antibody reaction will not be achieved.

Furthermore, conventional immunoassay techniques have drawbacks of usually taking a long time and not being able to measure automatically a large amount of samples.

Used for the quantitative analysis of specific antigens or antibodies present in a sample is, for example, radio immunoassay (hereinafter "RIA"). Since, however, a radioactive element is employed in RIA, it has the problems that an equipment for its exclusive use must be installed, operation must be carried out by a qualified operator and, moreover, waste is required to be disposed with caution.

Known as another analytical method is, for example, immunoelectrophoresis. The immunoelectrophoresis, however, has the problems that it requires a long time for the assay, has a low sensitivity, and can not be applied when there is contained only a very trace amount of target substances (or substances to be detected).

Now, in an earlier Japanese Patent Application No. 224509/1983, the present inventors have disclosed a liposome reagent comprising a hydrophilic antibody or antigen immobilized on its surface and a hydrophilic marker material enclosed in its inside. The analytical method employing this reagent can be summarized as follows: The above liposome reagent is added to the sample in which antigens or antibodies are present and a complement is separately added thereto, so that liposomes are destroyed by the antigen-antibody reaction and by the action of the complement to be accompanied with it and the marker materials enclosed (for example, fluorescent chemical substances) are released. Since there is a correlation between the quantity of this marker materials released and the quantity of the target substances in the sample, the target substances can be determined by determining the released marker materials according to a given analytical method (for example, a fluorescent analysis). Employment of this reagent may cause no problems that may be caused in RIA, and thus the immunoassay can be expected to be simplified.

However, when a sample containing serum or protein is analyzed with use of this liposome reagent, it has come to be found that a nonspecific reaction takes place independent of the antigen-antibody reaction to cause the destruction of liposomes. This is presumed to be caused by the reaction between the protein or trace chemical substances and the liposomes. For this reason, it has been conventionally practiced that the sample such as a serum is diluted to carry out the analysis.

For example, when a reagent comprising an anti-human alpha-fetoprotein antibody (hereinafter "anti-human AFP antibody") immobilized on liposomes is used to analyze AFP in serum, it has been practice to dilute human serum to 1/100 in order to eliminate the influence by the nonspecific reaction. However, a normal human serum contains only $10^{-8}$ g/ml or less. Therefore, the dilution of normal human serum to 1/100 may result in the measurement corresponding to an AFP concentration of $10^{-10}$ g/ml or less (for example, the fluorescent analysis), bringing about the problem that a precise determination can be hardly carried out.

SUMMARY OF THE INVENTION

An object of this invention is to provide a method for an immunoassay of a homogeneous system by which an antigen or antibody in a sample can be quantitatively measured in a short time without any separating operations by using a developed reagent for the immunoassay in which a hydrophilic antigen or antibody is supported on liposomes.

As discussed in the above, a conventional immunoassay has involved the problems that liposomes are destroyed by the nonspecific reaction or precise and simple determination can not be achieved.

Accordingly, an object of this invention is to provide an immunoassay capable of carrying out a precise and simple analysis.

The present inventors have intensively conducted research to achieve the above-mentioned object, and as a result, they have now succeeded in immobilizing the antibody, at least a part of the antibody or antigen corresponding to the antigen or antibody in a sample on liposomes which will be dissolved by a function of complement, without lowering the activity of the antibody or antigen, and have found out that the object of this invention is achieved by enclosing a marker material in the liposomes. The completion of this invention has just been accomplished on the basis of these research results.

That is to say, the reagent used with complement to analyse an antigen or antibody in a sample for immunoassay of this invention comprises liposomes; a hydrophilic antigen, antibody or at least a part of the antibody immobilized on the liposomes by a cross-linking method or an active lipid method; and a hydrophilic marker material enclosed in the liposomes.

Further, this immunoassay comprises by mixing, with a sample including an antigen or antibody and a complement, a reagent for the immunoassay comprising liposomes, a hydrophilic antigen, antibody or at least a part of the antibody immobilized on the liposomes by a cross-linking method or an active lipid method, and a hydrophilic marker material enclosed in the liposomes; and measuring the marker material released from the liposomes in order to quantitatively determine the antigen or antibody concentration in the sample.

The immunoassay of this invention employs an immunoassay reagent comprising liposomes consisted of at least any one of phospholipids and glycolipids, a marker material enclosed in said liposomes, and an antibody or part of the antibody, or an antigen immobilized on said liposomes by a cross-linking method, and comprises bringing said immunoassay reagent into contact with a sample, wherein a material for preventing nonspecific lysis of the liposomes (hereinafter "blocking material") is made present together in a reaction mixture to carry out the subsequent immune reaction.

According to the immunoassay of this invention, a functional group for immobilization, remaining on liposomes after an antibody or part of the antibody, or an antigen, have been immobilized is blocked in the immune reaction mixture by said blocking agent, thus causing no nonspecific reaction with, for example, proteins or trace substances in the serum serving as a sample. Accordingly, it is unnecessary to excessively dilute the target substances, and made possible to carry out a precise quantitative analysis, also with simplified operation.

BRIEF DESCRIPTION OF THE DRAWINGS

FIGS. 11 and 11A–11E are graphs showing the relative release rate of liposomes in a normal human serum base, without and with increasing added amounts of cysteine.

DESCRIPTION OF THE PREFERRED EMBODIMENTS

Figure 1:
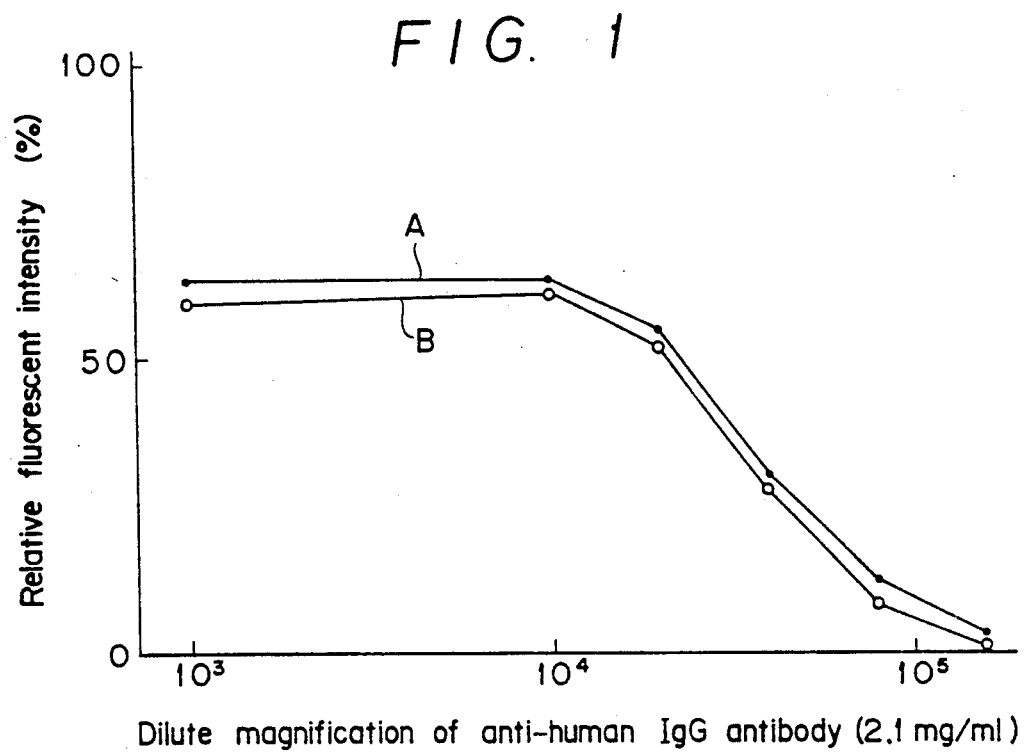
FIG. 1 is a diagram showing the correlation between a dilute magnification of an anti-human IgG antibody and a relative fluorescent intensity in the case that the anti-human IgG antibody was determined using IgG immobilized liposomes.

In this invention, the blocking material refers to a material for preventing the nonspecific lysis of liposomes that originates from the composition of liposomes, particularly an antibody-immobilizing functional group made present in lipid membranes of liposomes, and is caused by the contact with a sample (for example, plasma, serum, celom liquid, urea, etc.).

The immunoassay reagent used in this invention can be prepared by, for example, the procedure as described below.

First, desired lipids are reacted with a cross-linking agent in a solvent to introduce functional groups in lipid molecules, thus forming functional lipids. This functional group acts as a functional group for immobilizing the antibody or part of the antibody, or the antigen, formed on the liposomes. Next, the resulting functional lipids, and, if necessary, cholesterol and other lipids in appropriate amounts are put in a flask, and dissolved and mixed by adding a solvent, followed by suction removal of the solvent to dryness. As a result, a lipid thin film is formed on the surface of the flask wall. Subsequently, an aqueous solution containing marker materials is added in the flask, which is stoppered and vigorously shaken to prepare a liposome suspension.

On the other hand, in the antibody or part of the antibody, or the antigen, immobilized on the liposomes, a cross-linking group is introduced if necessary by the reaction with a cross-linking agent, followed by modification by treatment with a reducing agent depending on the necessity.

Subsequently, the above liposome suspension is reacted with the antibody or part of the antibody, or the antigen, in a suitable buffer to immobilize the antibody or part of the antibody, or the antigen, on the liposomes.

In the immunoassay reagent of this invention, the liposomes are comprised of at least any one of phospholipids and glycolipids. Also, as described above, 100 to 500 mol % of cholesterol may be added to the phospholipids or glycolipids if necessary, whereby there can be obtained stable liposomes. The carbon chain of the fatty acid in the phospholipids or glycolipids may preferably have the carbon atom of 12 to 18, more preferably of an even number.

In the immunoassay reagent of this invention, the marker material to be enclosed in the liposomes is selected from hydrophilic materials and can be determined when released the liposomes. Such materials may include, for example, fluorescent substances such as carboxyfluorescein, calcein and Rhodamine B which give no fluorescence at a high concentration because of self quenching but emit a very intensive fluorescence at a low concentration ($10^{-4}$ M or less); luminous substances such as luminol and luciferin which emit owing to an oxidative reaction outside the liposomes; absorptive compounds having absorption bands specific to a visible region or ultraviolet region (such as water-soluble dyes); saccharides such as glucose and sucrose which are decomposed by the action of an oxidase to bring about the consumption of oxygen or formation of hydrogen peroxide; relatively great ionic compounds such as tetrapentyl ammonium chloride; coenzymes such as nicotinamide adenine dinucleotide (NAD); radical compounds such as methylviologen; etc. These chemical substances are suitably selected taking account of the factors such as the detecting method, the sensitivity and the stability of liposomes.

In the immunoassay reagent of this invention, the antibody or part of the antibody, or the antigen, immobilized on liposomes can be arbitrarily selected from proteins or peptides (for example, immunoglobulins such as IgG, IgE, IgD, IgA and IgM; enzymes such as transaminase, lactate dehydrogenase and creatine phosphokinase; tumor markers such as alpha-fetoprotein and carcinoembryonic antigens (CEA); peptide hormones such as insulin and growth hormones; etc.), carbohydrates (for example, all sorts of Lewis antigens, Forssman antigens and microbiological cell wall polysaccharides), substances relating to nucleic acid (for example, polynucleotide, nucleotide, nucleoside, etc.), lipids (for example, lipoprotein, cardiolipin, etc.), and other low molecular substances (such as steroid hormone, thyroxine, all sorts of drugs, etc.), depending on the subject for the assay. Here, except for the low molecular antigens (haptens) that can not derive antibodies by themselves, the antibody, or part of the antibody, such as IgG or IgM corresponding to the respective antigen may preferably be immobilized on the liposomes.

In the immunoassay reagent of this invention, the cross-linking agent with which the reaction with lipid molecules is carried out in order to introduce the immobilizing functional groups in the liposomes, or the cross-linking agent used for optionally introducing the cross-linking groups in the antibody or part of the antibody or the antigen, may include, for example, N-succinimidyl-3-(2-pyridyldithio)propionate (SPDP), N-succinimidyl-4-(p-maleimidophenyl)butyrate (SMPB), N-succinimidyl-4-(p-maleimidophenyl)acetate (SMPA), N-succinimidyl-4-(p-maleimidophenyl)propionate (SMPP), N-(γ-maleimidobutyryloxy)succinimide (GMBS), N-(ε-maleimidocaproyloxy)succinimide (EMCS), disuccineimidylsuberate (DSS), glutaraldehyde (GA), phthalaldehyde, terephthalaldehyde, phthalic acid, terephthalic acid and an aliphatic dicarboxylic acid represented by the chemical formula:

$$HOOC-(CH_2)_n-COOH \quad (n=1 \text{ to } 10)$$

For example, SPDP is represented by the formula:

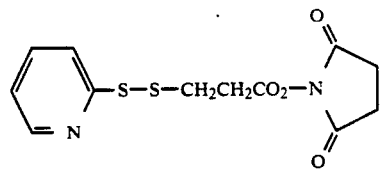

which is a hetero-bifunctional reagent capable of reacting under mild conditions and used for making formation into a thiol and for producing an intramolecular (cross-linking) coupled compound.

When the cross-linking agent is reacted to introduce the cross-linking group in the antibody or part of the antibody, or the antigen, it may sometimes become necessary to modify the cross-linking group by the reducing treatment as mentioned above.

When SPDP is used as the cross-linking agent, the dithiopyridyl group (DTP) remaining on the liposome side causes a nonspecific reaction with a sample. The blocking agent herein used refers to a chemical substance having the action of reduction that brings the disulfide bond of DTP into cleavage. Said reducing chemical substance may generally be a chemical substance having an SH group, and specifically be selected from dithiothreitol, 2-mercaptoethanol, cysteine, cysteamine, glutathione, etc. Also, in this instance, 2-mercaptoethanol, cysteine, etc. are more suited as the blocking agent of this invention. This blocking agent can be used in concentration of 0.1 to 10 $\mu M$, and preferably 1 to 2 $\mu M$ in the instance of 2-mercaptoethanol or cysteine. Various methods can be contemplated as methods for adding the present blocking agent, but the sample may be directly diluted with the present blocking agent, or the latter may be separately added when the sample is brought into contact with liposomes.

The immunoassay of this invention is carried out in the following manner. Namely, a sample containing target substances is first mixed with an isotonic solution containing the blocking agent. Here, the rate of dilution of the sample is selected depending on the assaying limit of the substances to be assayed.

In this sample and the blocking agent, the immunoassay reagent comprised of liposomes is added, and the complement is separately added thereto. In this occasion, there may be also used a method in which a second antibody against the target substance is added to catch the target substance from both sides. If necessary, the second antibody and/or complement can be diluted with the isotonic solution containing the blocking agent. As a result thereof, the liposomes are destroyed by the antigen-antibody reaction between the target substance and the antibody or part of the antibody, or the antigen, immobilized on the liposomes and by the action of the complement to be accompanied therewith, and thus the marker material (for example, a fluorescent compound) enclosed therein is flowed out. Since there is a correlation between the quantity of the thus released marker material and the quantity of the target substance in the sample, the determination of the released marker material by a suitable analytical method (for example, a fluorescent analysis) can determine the target substance.

In an actual quantitative analysis, a calibration curve is beforehand prepared by using a target substance of known concentration, and the quantitative analysis is carried out on the basis thereof and by the reaction with the target substance of unknown concentration.

The time required for sufficient reaction between the immunoassay reagent of this invention and the target substance may vary depending on the kind of the target substance, properties of liposomes, reaction conditions, and also the kind, purity, immobilization form, etc. of the antibody or part of the antibody, or the antigen, immobilized on the liposomes. For this reason, desired is to carry out a preliminary assay by using a sample previously prepared to have a given concentration and containing substances of the same kind with the target substances, to thereby set an optimum time for the reaction between the immunoassay reagent and the target substances.

The target substances that can be determined by the immunoassay reagent of this invention may include tumor markers such as AFP (alpha-fetoprotein), BFP (basic fetoprotein), CEA (carcinoembryonic antigen) and POA (pancreatic oncofetal antigen), immunoglobulins (such as IgG, IgE, IgD, IgA and IgM), hormones (such as insulin and $T_3$) and drugs, covering over a wide range.

Liposomes for an immunoassay of this invention have a wide meaning including even a red blood cell ghost membrane. As such liposomes, any ones are acceptable so long as it has been conventionally used, but the liposomes composed of a phospholipid or glycolipid and cholesterol are more preferable from the viewpoint of the stability of the reagent. For example, when synthesized from the phospholipid and cholesterol, the particularly stable liposomes can be prepared on the condition that the molar ratio of phospholipid : cholesterol is between 1:0.1 and 1:5.0, more preferably 1:1 or so. As for a fatty acid residue in the phospholipid, the number of its carbon atoms is preferably 12 to 18, and it is more preferable that this number is even. Further, in cases that glycolipid is substituted for phospholipid or both of phospholipid and glycolipid are used, the molar ratio of these lipids to cholesterol is preferable in the range as mentioned above.

Antigens, antibodies or at least a part of the antibody to be immobilized on the liposomes include antigens for tumor markers (the above-mentioned AFP, BEP, CEA, POA, etc.), immunoglobulins (IgA, IgE, IgG, IgM, etc.), hormones (insulin, $T_3$, $T_4$, etc.), drugs (phenitoin, digoxin, etc.) and the like; or antibodies against the aforesaid antigens. However, these antigens, antibodies or at least a part of the antibodies are required to be hydrophilic.

In the reagent of this invention, the antigen, antibody or at least a part of the antibody is immobilized on the liposomes by using a cross-linking agent or an activator for a lipid with the aid of a covalent bond between atoms.

In this invention, an amount of the phospholipid and/or glycolipid constituting the liposomes is preferably such that an amount of the above compound which has reacted with the cross-linking agent is within the range of 0.01 to 30 mol %, in the case a cross-linking method is employed. Further, it is preferred that a concentration of the hydrophilic antigen, antibody or at least a part of the antibody to be immobilized is within the range of 0.01 to 20 mg/ml with respect to 0.5 mM of the liposomes in terms of the lipid.

When the amount is out of above range, a prepared reagent is not applicable for practical use since the sentivity for measurement and stability of the prepared liposomes are greatly affected depending on an amount of the lipid to be reacted with cross-linking agent and a concentration of a protein to be immobilized.

In the reagent of this invention, the antigen, antibody or at least a part of the antibody is immobilized on the liposomes by using an undermentioned cross-linking agent such as N-succinimidyl-3-(2-pyridyldithio)propionate with the aid of a covalent bond between atoms.

The marker material to be enclosed in the liposomes must be hydrophilic and must be determinable when released out of the liposomes. Examples of such marker materials include fluorescent compounds such as carboxy fluorescein which emits no fluorescence due to self quenching at a high concentration but gives off a very intensive fluorescence at a low concentration ($10^{-3}$ M or less); luminous compounds such as luminol and luciferin which emit light owing to an oxidative reaction outside the liposomes; saccharides such as glucose and sucrose which are decomposed by the function of an oxidative fermentation in order to lead to the consumption of oxygen or the production of hydrogen peroxide; relatively great ionic compounds such as tetrapentyl ammonium; coenzymes such as nicotinamidoadeninedinucleotide (NAD); radical compounds such as methylviologen; absorptive compounds having absorption bands specific to a visible region or ultraviolet region such as water-soluble metallic indicators, e.g Xylenol Orange (XO), Methylxylenol Blue (MXB), Methylthymol Blue (MTB), water-soluble PADAP (5-Br-PAPS), water-soluble PADAB (5-Br-PSAA), Bismuthiol II, Pyrocatechol Violet (PV) and Eriochrome Black T (BT), and water-soluble dyes, e.g.

Rhodamine B, Oxamine Red X and Acid Orange I; and enzymes such as alkaline phosphatase, glucose oxidase, peroxidase, luciferase and the like.

These compounds mentioned above can be suitably selected taking into consideration, factors such as a detecting manner, a sensitivity and a stability of the liposomes.

The reagent for the immunoassay regarding this invention can react with the antigen or antibody to be detected, which is included in the sample, and the separately added complement in order to discharge a marker material from inside of the liposomes. Then, the discharged maker material is measured by means of a method with respect to the discharged marker material, whereby the quantitative analysis of the antibody or antigen included in the sample can easily be carried out.

The reagent for the immunoassay of this invention described hereinbefore can be prepared, for example, in the following method: First of all, a desired lipid is reacted with a cross-linking agent (a method of using such a cross-linking agent is called a cross-linking method) in a solvent (in place of the cross-linking agent, an activator for the lipid may be used, and a method of using such an activator is called an active lipid method), and functional groups which will be able to combine with the antigen, antibody or at least a part of the antibody immobilized on the liposomes are introduced into the lipid molecules. Next, the thus obtained functional lipid, cholesterol and, if necessary, another lipid are placed in a flask, and a solvent is further added thereto. After mixing, evaporation for the removal of the solvent and suction to dryness are followed. Subsequently, a selected aqueous marker material solution is added to the flask on the inner wall surface of which a thin membrane is formed, and it is sealed with a cap. After stirring, a suspension of the immobilized liposomes is prepared.

On the other hand, the antigen, antibody or at least a part of the antibody to be immobilized on the liposomes is reacted with the cross-linking agent in a buffer solution to introduce cross-linking groups thereinto. After this step, if necessary, the antigen or antibody is further reacted with a reagent (e.g., dithiothreitol (DTT)) for reducing the cross-linking groups, thereby obtaining the modified antigen, antibody or at least a part of the antibody. This process can be omitted, when the lipid is treated with its activator in the preceding process.

In the last place, the immobilized liposomes are reacted with the modified antigen, antibody or at least a part of the antibody (in the case that the active lipid method is employed, the unmodified antigen, antibody or at least a part of the antibody) in the buffer solution in order to prepare the reagent for the immunoassay of this invention. In general, such a reagent is obtained in the form of liposomes which include the marker material therein and support the immobilized antigen, antibody or at least a part of the antibody on the surfaces thereof. At this time, it is important to suitably vary a concentration of the immobilized modified antigen, antibody or at least a part of the antibody in compliance with a kind of target to be measured.

Examples of the cross-linking agents used in the above-mentioned cross-linking method include N-succinimidyl-3-(2-pyridyldithio)propionate (SPDP), N-succinimidyl-4-(p-maleimidophenyl)butyrate (SMPB), N-succinimidyl-4-(p-maleimidophenyl)acetate (SMPA), N-succinimidyl-4-(p-maleimidophenyl)propionate (SMPP), N-(γ-maleimidobutyryloxy)succinimide (GMBS) and N-(ε-maleimidocaproyloxy)succinimide (EMCS).

The above compound SPDP is represented by the following formula:

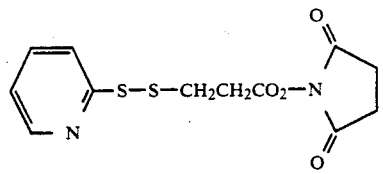

This compound SPDP reacts under moderate conditions to couple compounds having primary amino groups to each other, and it is commercially available from Pharmacia Inc. This cross-linking agent can be utilized, for example, as follows: The protein antigen to be immobilized is treated with the agent SPDP and is reduced with dithiothreitol (DTT). Then, it is reacted with the liposomes which has previously been treated with SPDP. After allowed to stand at room temperature or less for a period of several hours to one day, the antigen can be immobilized on the liposomes.

The above-mentioned compound SMPB is represented by the following formula:

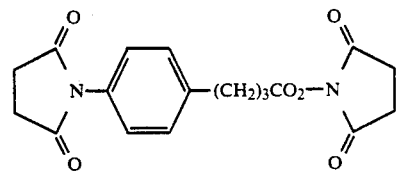

This compound SMPB can immobilize a protein by a reaction similar to that of SPDP. However, in the case of SMPB, an —S—S— bond is not included in the end product (an —S— bond is only included therein). Thus, the end product is stable even under a reducing atmosphere such as in a serum.

On the other hand, examples of the activators for the lipids include cyanogen bromide (CNBr), cyanuric chloride (CC), epichlorohydrin (EH), O-bromoacetyl-N-hydroxysuccinimide and 1,4-bis(2,3-epoxypropoxy)-butane (BEPB). Of these compounds, CNBr, CC, EH and BEPB serve to activate compounds having saccharide residues and to couple them to compounds having primary amino groups. Therefore, when the saccharide residues are present on the liposomes, these reagents can be applied. Also in the case that the antigen itself is a glycoprotein and the primary amino groups are present on the liposomes, these activators are likewise effective.

If the cross-linking agents or the activators for the lipids which have been mentioned hereinbefore are employed, the immobilization of the hydrophilic antigen, antibody or at least a part of the antibody on the liposomes will be feasible, though such an immobilization has been impossible in former days. In the method of this invention, there can be avoided such a phenomenon as the deterioration in the activity of the antigen or antibody at the time of the immobilization with a strong cross-linking agent, e.g., glutaraldehyde (hereinafter referred to as GA).

Moreover, the reagent for the immunoassay of this invention may be manufactured by first coupling the lipid to the antigen, antibody or at least a part of the antibody with the aid of the cross-linking agent or the activator for the lipid; adding the coupled material together with a surface active agent to water in order to form micelles; and removing the surface active agent therefrom by means of dialysis or gel filtration.

Materials which can be determined by the above-mentioned reagent for the immunoassay widely range and include antigens of tumor markers (the above-mentioned AFP, BEP, CEA, POA, etc.), immunoglobulins (IgA, IgE, IgG, IgM, etc.), hormones (insulin, $T_3$, $T_4$, etc.), drugs (phenitoin, digoxin, etc.) and the like; and antibodies or at least a part of the antibodies corresponding to the aforesaid antigens. These materials to be detected which will bring about an antigen-antibody reaction with the immobilized antigen, antibody or at least a part of the antibody may hot always be hydrophilic.

According to the method for the immunoassay of this invention, the reagent for the immunoassay described above is mixed with a sample including the antigen or antibody (if the antigen is immobilized on the liposomes, the antibody sample will be used; if the antibody or at least a part of the antibody is done, the antigen sample will be used) and a complement in a suitable buffer solution (e.g., a gelatin-Veronal buffer solution [hereinafter referred to as $GVB^-$] including, at ultimate concentrations, 0.1 mM $MgCl_2$ and 0.15 mM $CaCl_2$, respectively) in order to bring about a coupling reaction of the antigen-antibody with the complement. Then, a marker material is released out of the liposomes in proportion of their reacting amount. Next, determination is carried out by an analytical method (e.g., if the marker material has fluorescence, a fluorescent analytical method will be emploed) in accordance with this marker material, and an amount of the antigen or antibody in the sample can be measured on the basis of a previously prepared calibration curve.

The complements used in the determining operation are not particularly limited, but the preferred complements each have a high activity, i.e. a high complement value and preferably in the range from 0.1 to 10 $HC_{50}$. Usually, a guinea pig serum is preferably employed. However, sera of rabbit, mouse, human and the like may also be applicable. In the determination of the antigen or antibody by the use of the reagent for the immunoassay of this invention, the complement value is an important factor to decide a measurement range and a detection limit, and better measurement results can be obtained by changing this complement value variously.

Further, if this invention is applied to the preparation of an analytical reagent in which a substrate or enzyme is immobilized on the liposomes, an enzyme or substrate in a sample can also be quantitatively analyzed.

According to the reagent for the immunoassay of this invention, the hydrophilic antigen, antibody or at least a part of the antibody is immobilized on the liposomes without deteriorating its activity, and since the marker material is enclosed in the liposomes, the accurate determination, having a high detection sensitivity, of the antigen or antibody can be carried out in a homogeneous system in a short time. In addition thereto, the analytical method of this invention can be applied to an extensive region of the materials to be detected and can be accomplished at lower costs. Further, the present invention permits facilitating a highly accurate automatic analysis in miniature and simultaneously measuring many components.

Now, this invention will be described in detail as examples, but these examples never intend to limit the scope of this invention.

EXAMPLE 1

Measurement (I) of an anti-human immunoglobulin G (IgG) antibody by the use of human IgG immobilized liposomes (A) Reagents and preparation of the immobilized liposomes (1) Reagents There were used dipalmitoylphosphatidyl choline (DPPC), cholesterol, dipalmitoylphosphatidyl ethanolamine (DPPE) and dithiothreitol (DTT) which were commercially available from Sigma Inc. N-succinimidyl-3-(2-pyridyldithio)propionate (SPDP) and Sephadex G-25 Fine were bought from Pharmasia Fine Chemicals Inc. Other reagents were commercially available ones (special grade), which were directly used without any purification. Further, ion-exchange exchange water was used as water.

(2) Preparation of the immobilized liposomes (a) Preparation of DPPE-dithiopyridinate (DPPE-DTP)

In a test tube were placed 5 ml of 10 mM DPPE (a chloroform solution) and 50 mg of SPDP, and after replaced with a nitrogen gas and sealing, reaction was carried out at room temperature for 2 hours. After the reaction, the reaction product was extracted three times with physiological saline in a five-fold amount, and the remaining chloroform phase was subjected to a vacuum drying treatment. At the last step, 5 ml of chloroform were added thereto, and the product was then stored in a sealed test tube at $-20°$ C.

(b) Preparation of the liposomes

All of a used lipid was dissolved in chloroform or a chloroform/methanol solution (2/1). In the first place, 200 µl of 5 mM DPPC, 100 µl of 10 mM cholesterol and 60 µl of 1 mM DPPE-DTP were placed in a 10 ml eggplant type flask and 2 ml of chloroform were further added thereto, followed by sufficient stirring. The used solvent was removed therefrom in a water bath (about 50° C.) by means of a rotary evaporator. Once again, 2 ml of chloroform were added thereto, and after enough stirring, the solvent was evaporated away by the rotary evaporator again. When this operation was repeated several times, a thin membrane was formed on the wall surface of the flask. The flask was then transferred into a desicator and suction was carried out for about one hour by a vacuum pump in order to absolutely remove the solvent. Next, 100 µl of 0.2M carboxyfluorescein (Eastman Kodak Inc.; pH 7.4) were added thereto, and the interior of the flask was replaced with nitrogen. After sealing, the flask was immersed in a water bath at 60° C. or so for about one minute. Continuously, vigorous stirring was carried out in the flask by a Vortex mixer till the thin lipid membrane on the wall surface thereof completely disappeared. By virtue of this operation, a liposomes suspension was prepared. A small amount of a buffer solution (GVB$^-$ including, at ultimate concentrations, 0.1 mM $MgCl_2$ and 0.15 mM $CaCl_2$, respectively; hereinafter merely referred to as $GVB^{2+}$) was added thereto, and all of the liposomes suspension was transferred to a centrifuge tube. Centrifugal treatment was carried out at 4° C. and 15,000 rpm for 20 minutes in order to remove free carboxyfluorescein. This treatment was repeated using $GVB^{2+}$ till the supernatant became transparent. In the last place, 2 ml of $GVB^{2+}$ and 5 μl of 10% $NaN_3$ were added thereto and were suspended by means of the Vortex mixer. After introducing nitrogen and sealing, the product was stored in a refrigerator.

(c) Modification of human IgG

In 2 ml of a 0.01M HEPES buffer solution (including 0.85% of NaCl; pH 7.45) were dissolved 5 mg of human IgG (available from Miles Inc.). After replaced with nitrogen, 10 μl of 10 mM SPDP (an ethanol solution) were added thereto. The resulting mixture was sufficiently stirred and was reacted for 30 minutes in situ. After the reaction, the reaction mixture was developed through a column (gel volume: about 15 ml) filled with Sephadex G-25 Fine gel which was previously saturated with a physiological saline, and elution was carried out with a 0.1M acetic acid buffer solution (including 0.85% of NaCl; pH 4.5). To a first peak fraction (about 2 ml) were further added 2 ml of the acetic acid buffer solution, and after replaced with nitrogen, about 30 mg of dithiothretol were added thereto. Reaction was carried out over enough stirring for 20 minutes. After the reaction, the reaction mixture was developed through a column (gel volume: about 30 ml) filled with Sephadex G-25 Fine gel which was previously saturated with a 0.01M HEPES buffer solution, and elution was carried out with the HEPES buffer solution. A first peak fraction (about 2 ml) was collected, and after nitrogen replacement, the product was stored in a refrigerator till used.

(d) Preparation of human IgG immobilized liposomes

The liposomes suspension prepared above was mixed with an equal amount of the modified human IgG solution, and after nitrogen replacement and sealing, reaction was carried out overnight at room temperature with slowly shaking, followed by washing with the HEPES buffer solution and next with $GVB^{2+}$ in order to remove unreacted human IgG. $GVB^{2+}$ in an amount equal to that of the liposomes suspesion used in the reaction, and 5 μl of 10% $NaN_3$ were lastly added, and after suspending and nitrogen replacement, the product was stored in a refrigerator till used.

(3) Measurement of an anti-human IgG antibody by the use of the IgG immobilized liposomes Into each of wells on a U-shaped plate (96 holes) made by Nunk Inc. were poured 25 μl of an anti-human IgG antibody which was diluted with a suitable amount of $GVB^{2+}$ 100-fold, and was poured into each well in an amount of 5 μl. In the last place, a complement (guinea pig serum) suitably diluted with $GVB^{2+}$ was added every 25 μl. Reaction was carried out at a constant temperature of 37° C. for 1.5 hours. After the reaction, 100 μl of a 0.01M EDTA-Veronal buffer solution were added to each well in order to stop the reaction, and a fluorescence of each well was measured by means of a fluorospectrophotometer for a plate (MFP-12F, available from Corona Electronic Co., Ltd.; Ex=490 nm, Em=520 nm). Measured values were represented with relative values by regarding, as 100%, a difference between a fluorescence of the well in which 25 μl of 10% Triton X-100 (available from Rohm & Haas Co.) were substituted for the antibody and that of the well in which 25 μl of $GVB^{2+}$ were substituted for the antibody. The results obtained by employing the 400-fold diluted complement (line A) and the 800-fold diluted complement (line B) are shown in FIG. 1, respectively.

EXAMPLE 2

Measurement (II) of an anti-human IgG antibody by the use of human IgG immobilized liposomes (1) Preparation of the immobilized liposomes Following the same procedure as in Example 1, the liposomes including carboxyfluorescein was prepared. After centrifugal washing, the liposomes were suspended in a 0.1M phosphoric acid buffer solution (including 0.85% of NaCl; pH 6.5) (2 ml), and 150 mg of DTT were then added thereto. After nitrogen replacement, stirring was sufficiently carried out and reaction was done at room temperature for 2 hours in situ. Washing was carried out (by using $GNV^{2+}$ already replaced with nitrogen) centrifugally (15,000 rpm, 20 minutes) and 5 μl of 10% of $NaN_3$ were added thereto, and the resulting product was stored in a refrigerator. On the other hand, an antigen was treated with SPDP in the same manner as in Example 1 and was separated by a gel filtration (elution with an HEPES buffer solution) and purified. The prepared liposomes suspension was mixed with the modified human IgG solution in equal amounts, and after nitrogen replacement, reaction was carried out overnight at room temperature with slowly shaking. After the reaction, washing was sufficiently done (by using $GVB^{2+}$ already replaced with nitrogen), and 5 μl of 10% $NaN_3$ were then added thereto. Afterward, the product was stored in a refrigerator. Incidentally, the liposomes which will be applied to the coupling reaction with modified human IgG is preferably treated with DTT just before the coupling step, but in the case that the liposomes coolingly stored is unavoidably used, it is preferred that a small amount (10 to 20 mg) of DTT is added thereto again before the coupling reaction and the reaction is then carried out at room temperature for 30 minutes or so. This process serves to cut off S-S bonds formed between the liposomes during the storage.

(2) Measurement of an anti-human IgG antibody by the use of the human IgG immobilized liposomes Following the same procedure as in Example 1, an anti-human IgG antibody was measured using the liposomes, and results similar to those of Example 1 were obtained.

EXAMPLE 3

Figure 2:
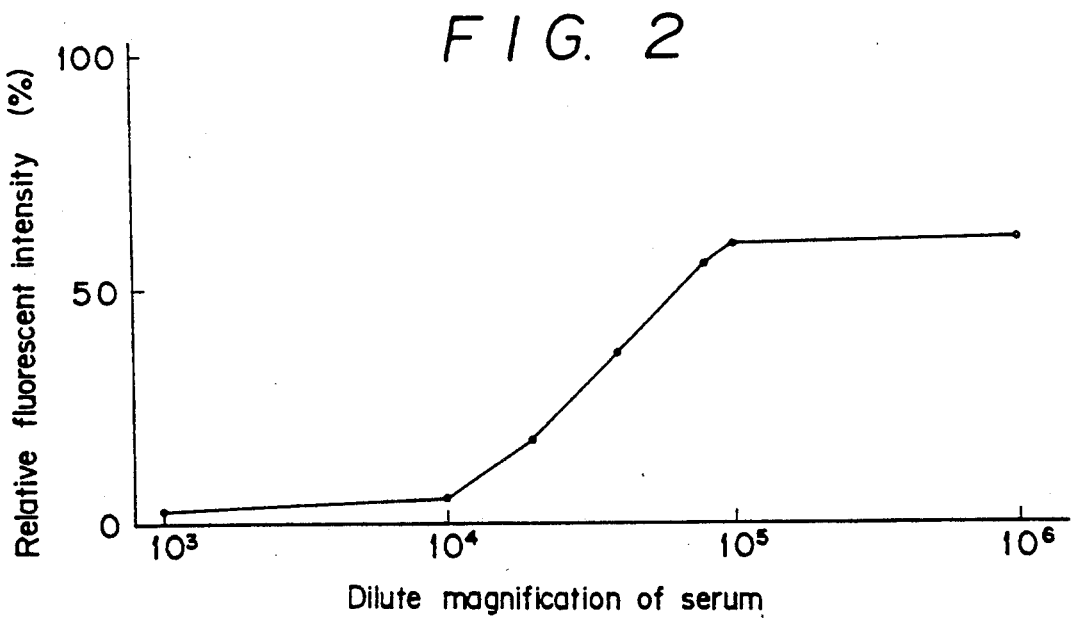
FIG. 2 is a diagram showing the correlation between a dilute magnification of a serum and a relative fluorescent intensity in the case that the human IgG in the serum was determined using human IgG immobilized liposomes.

Measurement of human IgG in a human serum by the use of the human IgG immobilized liposomes The liposomes, prepared in Example 1, on which human IgG was immobilized was utilized to measure an amount of human IgG in the human serum. Into each line on a microtiter plate, a 1,000-fold, a 10,000-fold and a 20,000-fold diluted (by using $GVB^{2+}$) anti-human IgG antibody were poured every 25 μl, and samples of human sera which were diluted 10 to $10^6$ times were added thereto every 25 μl. Reaction was then carried out overnight at 4° C. Next, the 100-fold diluted liposomes on which human IgG was immobilized was added thereto every 5 μl and a 400-fold or a 800-fold diluted complement (guinea pig serum) was lastly added thereto every 25 µl, and the resulting mixture was allowed to stand at 37° C. for 1.5 hours. Subsequent procedures were the same as described in the preceding paragraph regarding the measurement of the anti-human IgG antibody in Example 1. The experimental results are shown in FIG. 2. On the other hand, a solution including human IgG of which concentration was known was utilized and similar procedures were repeated in order to prepare a calibration curve with respect to the concentration of human IgG. An amount of human IgG in the human serum could be determined by utilizing this calibration curve.

EXAMPLE 4

Measurement of human AFP by the use of a human AFP immobilized liposomes

Following the method described in Example 1, human AFP (commercially available from Nippon Biotest Laboratory) was immobilized on the surface of liposomes including carboxyfluorescein. On the other hand, in the same manner as in Example 3, a suitably diluted (100 to 1000 ng/ml) (by using $GVB^{2+}$) anti-human AFP antibody solution was poured every 25 µl into wells on a microtiter plate, and a human AFP standard solution (3 to 1000 ng/ml; available from Nippon Biotest Laboratory) were added every 5 µl to each pair of two wells. Then, reaction was carried out at room temperature (about 25° C.) for 30 minutes. Afterward, 5 µl of the above-mentioned human AFP immobilized liposomes (which was diluted 100 times with $GVB^{2+}$) and guinea pig serum (which was diluted 400 times with $GVB^{2+}$) were added thereto, and the resulting mixture was allowed to sand at 37° C. for 1.5 hours. After that, 100 µl of an EDTA solution were added thereto to stop the reaction. Fluorospectrophotometer was employed for the determination of fluorescence in each well and the measured values were plotted with respect to a concentration of human AFP. For example, when the 100 ng/ml anti-human AFP could be quantitatively anaylzed within the range of 10 to 500 ng/ml. A concentration of AFP in an unknown sample could be determined by using a calibration curve within such a range.

EXAMPLE 5

Immobilization of human IgG on the liposomes including CNBr-activated hematoside (glycolipid)

(1) Preparation of the CNBr-activated hematoside

In 30 ml of chloroform/methanol (2:1) were dissolved 50 mg of hematoside ($GM_3$), and 5N NaOH was dropwise added thereto in order to adjust a pH of the solution to 10.5. While the solution was stirred by a stirrer, 1 g of CNBr (which was dissolved in several milliliters of methanol) was added thereto, and 5N NaOH was immediately added thereto in a dropwise manner in order to adjust its pH into a range of 10 to 11. After several minutes, the reaction mixture was transferred to a separatory funnel and 5 ml of distilled water were added thereto, followed by vigorous stirring. After 10 minutes, an lower layer therein was taken out to obtain CNBr-activated hematoside.

(2) Immobilization of human IgG on the liposomes

The liposomes were prepared in the same manner as in Example 1, and 5 mg of human IgG were added to this liposomes suspension. Reaction was carried out at room temperature for 3 hours. After washing with $GVB^-$, the liposomes were suspended in 2 ml of $GVB^-$ again and were then preserved in a refrigerator after the introduction of nitrogen.

(3) Quantitative analysis of anti-human IgG antibody (rabbit)

As a result of the quantitative analysis of the antibody in all the same procedure as in Example 1, it was definite that the determination of the antibody is feasible within the range of $10^{-8}$ to $10^{-10}$ g/ml.

EXAMPLE 6

Measurement (I) of an anti-human IgG antibody by the use of human IgG immobilized liposomes (A) Reagents and preparation of the liposomes (1) Reagents The used reagents were the same as in Example 1.

(2) Preparation of the immobilized liposomes (a) Preparation of DPPE-dithiopyridinate (DPPE-DTP)

In a conical flask equipped with a stopper were placed 70 g of DPPE, and the latter was dissolved in 25 ml of a chloroform/methanol (5:1) solution. After the addition of 60 ml of triethanolamine and 50 mg of SPDP, nitrogen replacement was carried out. Reaction was carried out at room temperature for one hour and the solvent was then removed from the system by means of a rotary evaporator. The resulting dried material was dissolved in 5 ml of a chloroform/methanol (10:1) solution and was purified with a silica gel column chromatography. The resulting product fractions were collected and were concentrated to about 5 ml by an evaporator. The yield was within the range of 80 to 95%. The storage was done at $-20°$ C. under the introduced nitrogen gas.

(b) Preparation of the liposomes

The procedure of the liposomes preparation in Example 1 was repeated with the exception that an amount of DPPE-DTP was 50 µl and an equal amount of 0.2M water-soluble PADAP (5-Br-PAPS) was substituted for carboxy fluorescein.

(c) Modification of human IgG

The procedure of the Example 1 was repeated with the exception that 5 mg of human IgG (available from Miles-Yeda Inc.) were used, and elution was carried out with the HEPES buffer solution. An initial protein fraction (about 2 ml) was collected, and after nitrogen replacement, it was stored in a refrigerator till used.

(d) Preparation of human IgG immobilized liposomes

The same procedure in Example 1 was repeated in order to prepare the liposomes on which human IgG was immobilized.

(3) Measurement of an anti-human IgG antibody by the use of the human IgG immobilized liposomes $GVB^{2+}$ ($GVB^-$ including, at ultimate concentrations, 0.1 mM $MgCl_2$ and 0.15 mM $CaCl_2$, respectively) having pH 7.8 was poured into cells every 25 µl. Next, the above-mentioned liposomes suspension was diluted with $GVB^{2+}$ 100-fold and was poured into each cell every 5 µl.

In the last place, a complement (guinea pig serum) suitably diluted with GVB$^{2+}$ was added thereto every 25 μl, and reaction was carried out at 37° C. for an hour. Measurement of the optical density was made at an absorption wavelength of 550 nm.

Figure 3:
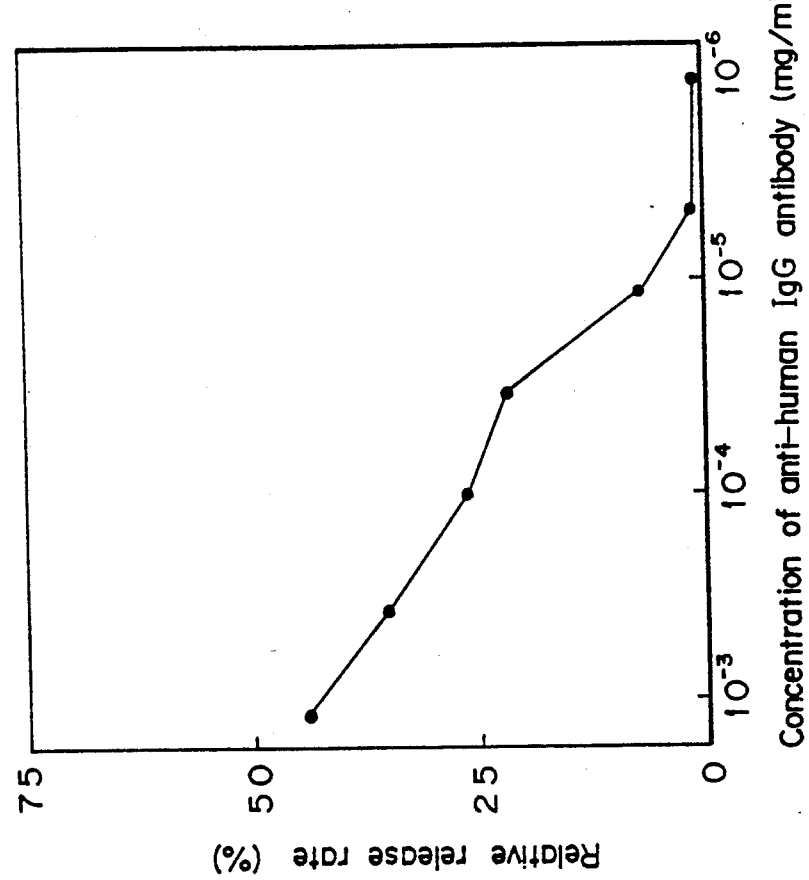
FIG. 3 is a characteristic diagram showing the correlation between a concentration of an anti-human IgG antibody and a relative release rate in the case that the anti-human IgG antibody was determined using human IgG immobilized liposomes.

The measured values were represented with relative values by regarding, as 100%, a difference between an absorption in the case that Triton X-100 and GVB$^{2+}$ were used in an amount of 25 μl, respectively, in place of the antibody and complement and an absorption in the case that 25 μl of GVB$^{2+}$ were used in place of the antibody. The results obtained by using the 400-fold diluted complement (complement value=0.5 CH$_{50}$) are shown in FIG. 3. This FIG. 3 indicates that the anti-human IgG antibody can be determined within the range of 10$^{-3}$ to 10$^{-5}$ mg/ml.

EXAMPLE 7

In all the same manner as in Example 1, liposomes on which human IgG was immobilized was prepared.

The measurement of an anti-human IgG antibody was made using these human IgG immobilized liposomes, as follows:

Into a U-shaped plate (96 holes) made by Nunk Inc. were poured 25 μl of an anti-human IgG antibody which was diluted with a suitable amount of GVB$^{2+}$. Next, the liposomes suspension was diluted with GVB$^{2+}$ 100-fold, and was poured into each well in an amount of 5 μl. In the last place, a complement (guinea pig serum) suitably diluted with GVB$^{2+}$ was added thereto every 25 μl. Reaction was carried out at a constant temperature of 37° C. for 1.5 hours. After the reaction, 100 μl of a 0.01M EDTA-Veronal buffer solution were added to each well in order to stop the reaction, and a fluorescence of each well was measured by means of a fluorospectrophotometer (MFP-12F, Corona Electronic Co., Ltd.) for the plate (Ex=490 nm, Em=520 nm). Measured values were represented with relative values by regarding, as 100%, a difference between a fluorescence of the well in which of 10% Triton X-100 and GVB$^{2+}$ were substituted in an amount of 25 μl respectively for the antibody and complement, and that of the well in which 25 μl of GVB$^{2+}$ were substituted for the antibody. The results obtained by employing the the 400-fold diluted complement (complement value=0.5 CH$_{50}$) are shown in FIG. 4.

Figure 4:
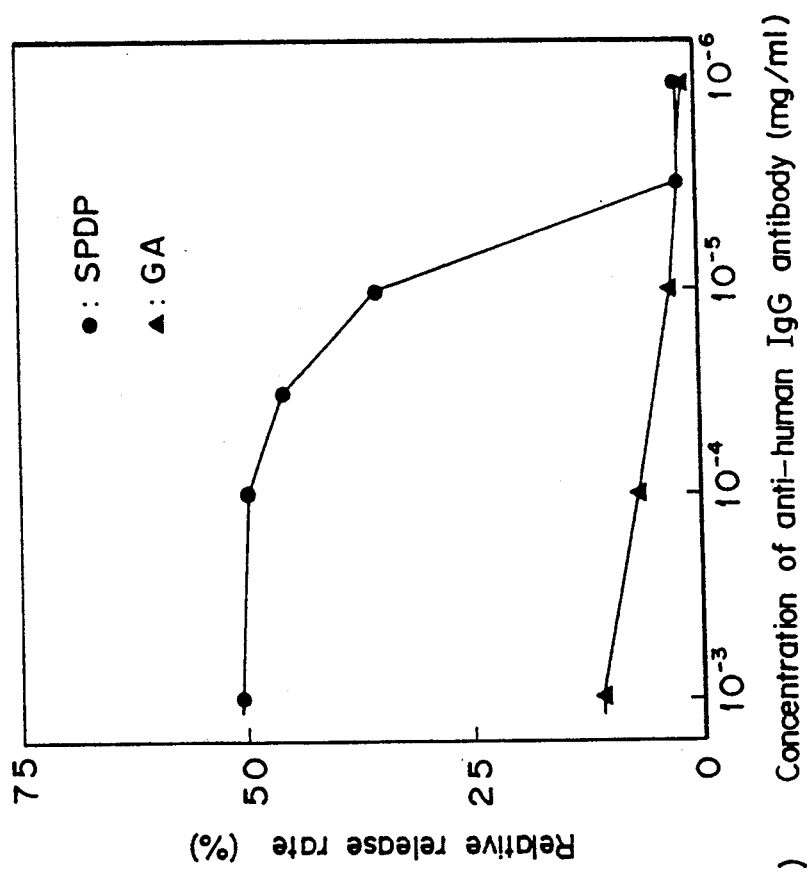
FIG. 4 is a characteristic diagram showing the correlation between a concentration of an anti-human IgG antibody and a relative release rate of a marker material in the case that the anti-human IgG antibody was determined using human IgG immobilized liposomes, where the curve a shows the case that SPDP was used as a cross-linking agent and curve b shows the case that GA was used.

The curve a in FIG. 4 shows a relation between a concentration of the anti-human IgG antibody included in the sample and a relative release rate of the marker material which was released by the reaction of the reagent for the immunoassay of this invention. As be apparent from the drawing, a definite relative relation as present between both of these factors, and thus the quantitative analysis of the sample is feasible on the basis of this fact. On the other hand, the curve b in the drawing exhibits a relation therebetween in the case that glutaraldehyde (GA) disclosed in conventional techniques was used as the cross-linking agent and the liposomes comprising DPPC, cholesterol and DPPE-DTP in a molar ration of 1:1:0.05 were employed. As the curve b indicates, the liposomes in which the conventional cross-linking agent was used scarcely changes the release proportion of the marker material in accordance with the variation of the sample concentration. By this fact, it has been confirmed that such liposomes cannot be applied to an accurate quantitative analysis.

EXAMPLE 8

Figure 5:
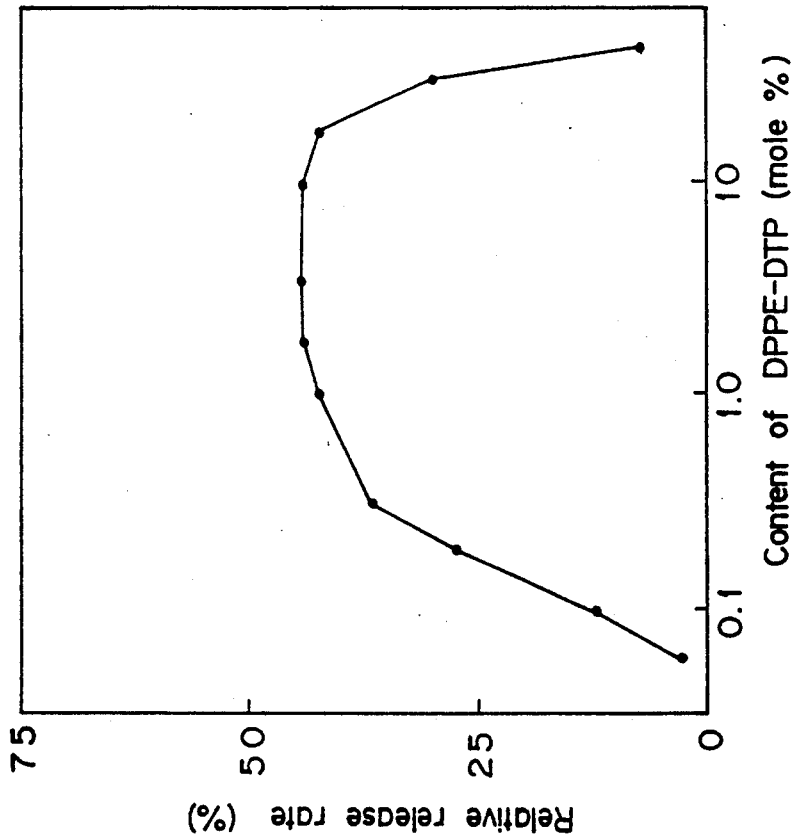
FIG. 5 is a characteristic diagram showing the correlation between a concentration of immobilized human IgG on a double membrane of the liposomes and a relative release rate of the marker material.

Following the procedure of Example 7, human IgG immobilized liposomes were prepared by changing a content of DPPE-DTP in the liposomes, in other words, by varying an amount of the lipid reacted with a cross-linking agent. The immobilized liposomes were measured for a release rate of CF from the immobilized liposomes when 2×10$^{-3}$ mg/ml of the anti-human IgG antibody and the 400-fold diluted complement (complement value=0.5 CH$_{50}$) were acted thereon. The results are shown in FIG. 5. As be apparent from this drawing, the release of CF was not observed at all in the case of the liposomes including no DPPE-DTP. In practice, a usable range was from 0.01 mol, and when the content of DPPE-DTP was increased, the CF release rate increased up to 1 mol %. however, when it was added in excess of this level, the CF release rate did not vary. Further, in the case of the liposomes including 30 mol % or more of DPPE-DTP, the spontaneous CF release was noticeably observed, and the stability was poor. By the results of this example, it was confirmed that constitutional ratios of the phospholipid and glycolipid reacted with the cross-linking agent are within the range of 0.01 to 30 mol %.

EXAMPLE 9

In Example 7, a concentration of human IgG was variously changed with it was immobilized on the liposomes comprising DPPC, cholesterol and DPPE-DTP in a molar ratio of 1:1:0.05, with the intention of inspecting a reactivity of the anti-human IgG antibody with the liposomes.

Figure 6:
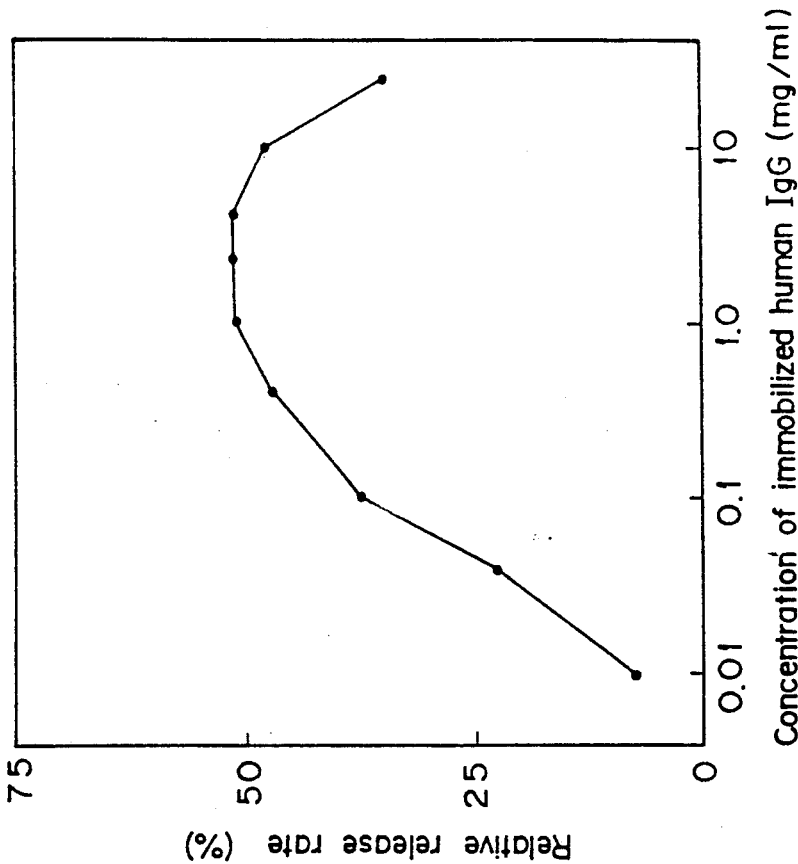
FIG. 6 is a characteristic diagram showing the correlation between a concentration of an immobilized human IgG antigen and a relative release rate of the marker material.

Concentrations of the antibody and complement were the same as in Example 8. The results are shown in FIG. 6. The liposomes on which no human IgG was immobilized did not react with the antibody at all. On the contrary, in the case of the liposomes on which the antigen was immobilized, an effective reaction to the antibody concentration of 0.01 mg/ml with respect to 0.5 mM of the liposomes in terms of an amount of the lipid used therein, to 20 mg/ml via a maximum point.

EXAMPLE 10

Figure 7:
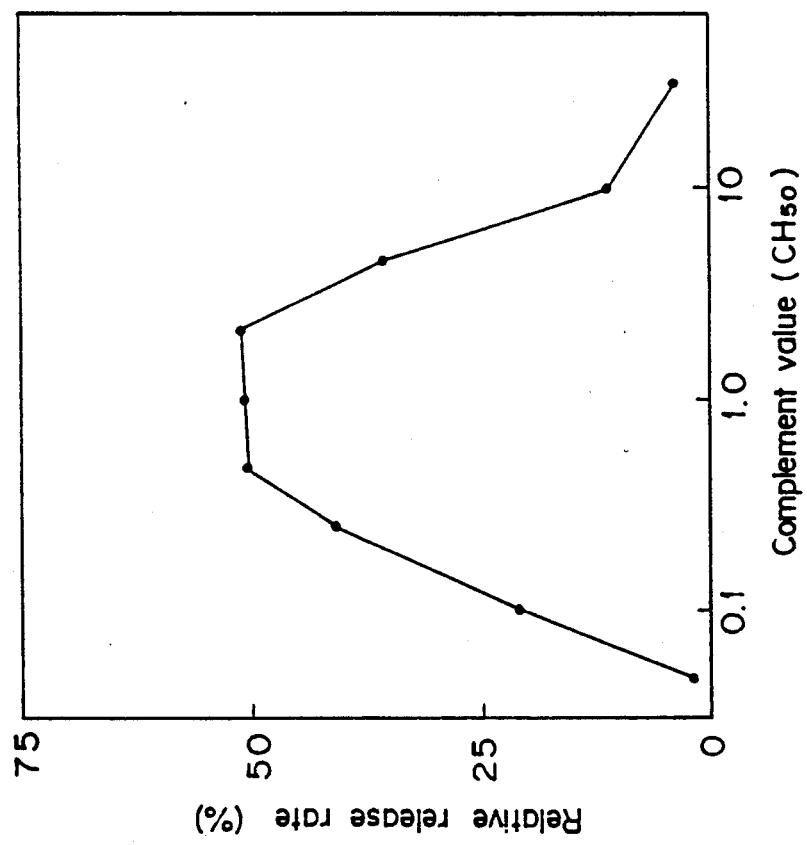
FIG. 7 is a characteristic diagram showing the correlation between a complement value and a relative release rate of the marker material.

A reactivity between the human IgG immobilized liposomes prepared in Example 7 and 2×10$^{-3}$ mg/ml of the anti-human IgG antibody was inspected by employing various complement values. As shown in FIG. 7, when the complement values were 0.1 CH$_{50}$, CF was released from almost all the liposomes even under conditions including no antibody. Therefore, it was impossible to detect the antibody.

As understood from the foregoing, by selecting the concentration of the cross-linking agent to be introduced into the liposomes, the concentration of the antigen and the complement value so that they may be within the range described in Example 7 to 10, a measurement system can be constituted in compliance with a material to be detected and its concentration.

EXAMPLE 11

Figure 8:
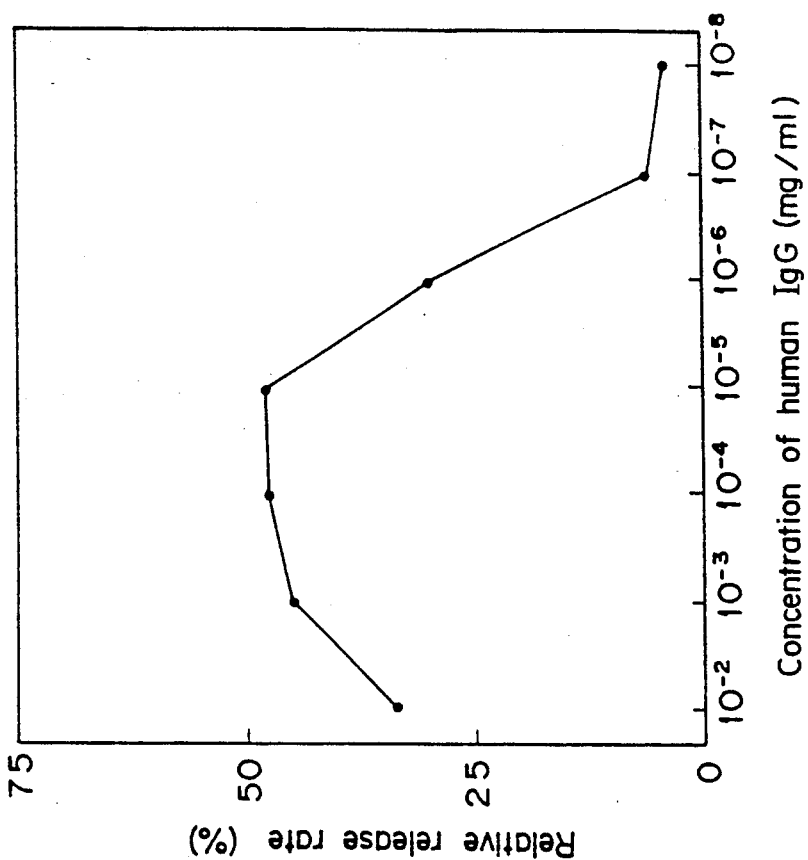
FIG. 8 is a characteristic diagram showing the correlation between a concentration of the human IgG antigen and a relative release rate of the marker material in the case that human IgG was measured using the anti-human IgG bearing-liposomes.

In the same manner as in Example 7, the liposomes on which an anti-human IgG antibody was immobilized was prepared. By the use of these liposomes, the determination of human IgG was carried out. In this case, a complement value was 2 CH$_{50}$. The results are shown in FIG. 8. It was confirmed that the determination of the antigen could be made also by using the antibody-immobilized liposomes, similarly to the employment of the antigen-immobilized liposomes.

Further, also by using liposomes on which an anti-human CEA antibody, an anti-human AFP antibody and the like are immobilized, antigens could be determined in a similar manner.

EXAMPLE 12

Figure 9:
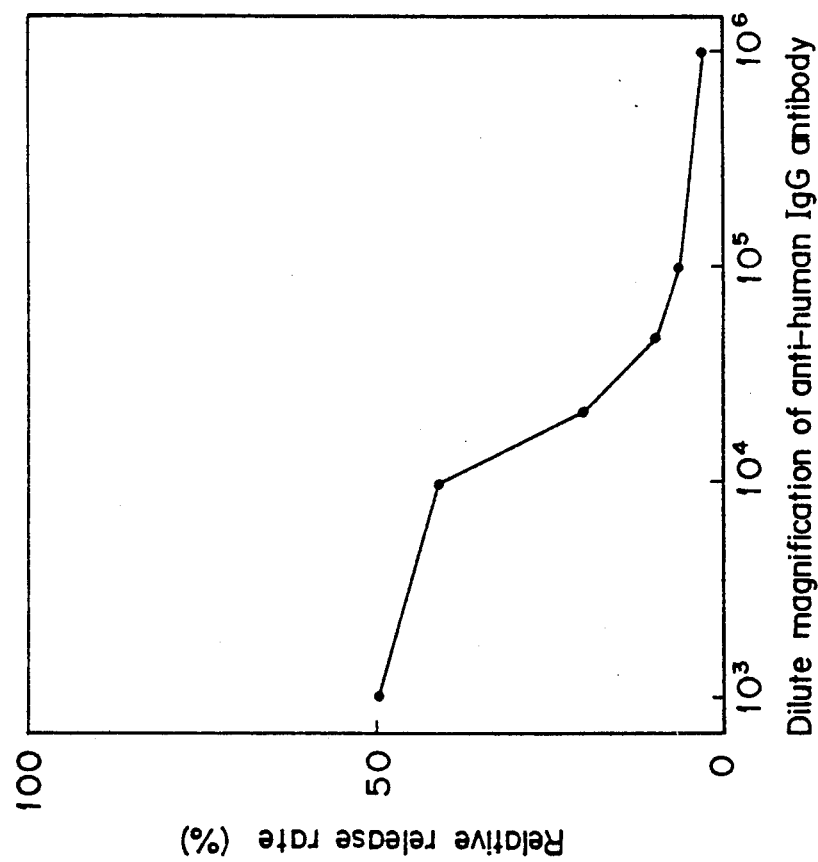
FIG. 9 is a characteristic diagram showing the correlation between a concentration of an anti-human IgG antibody and a relative release rate of a marker material in the case that the anti-human IgG antibody was determined using the human IgG bearing-liposomes which was enclosed glucose oxydase as the marker material.
Figure 11B:
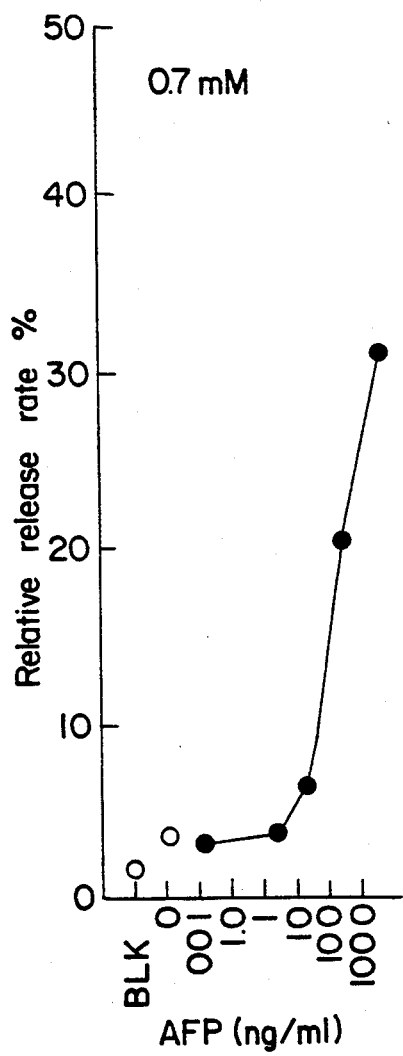
Figure 11C:
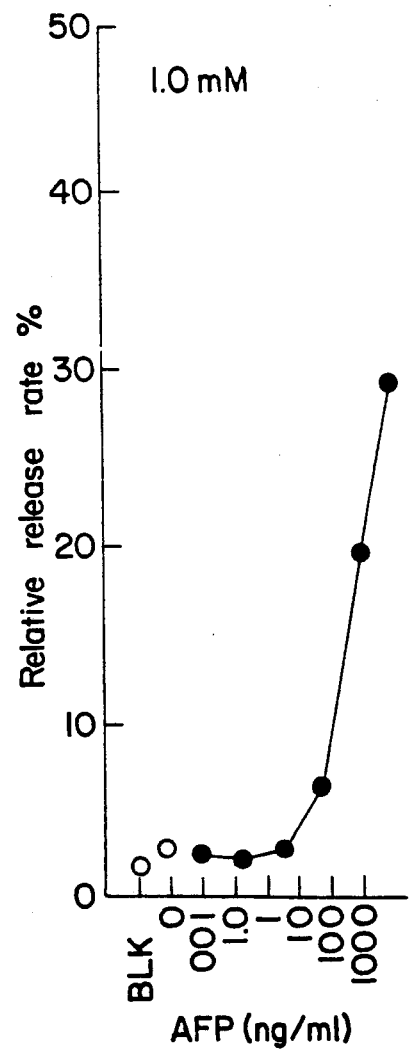
Figure 11D:
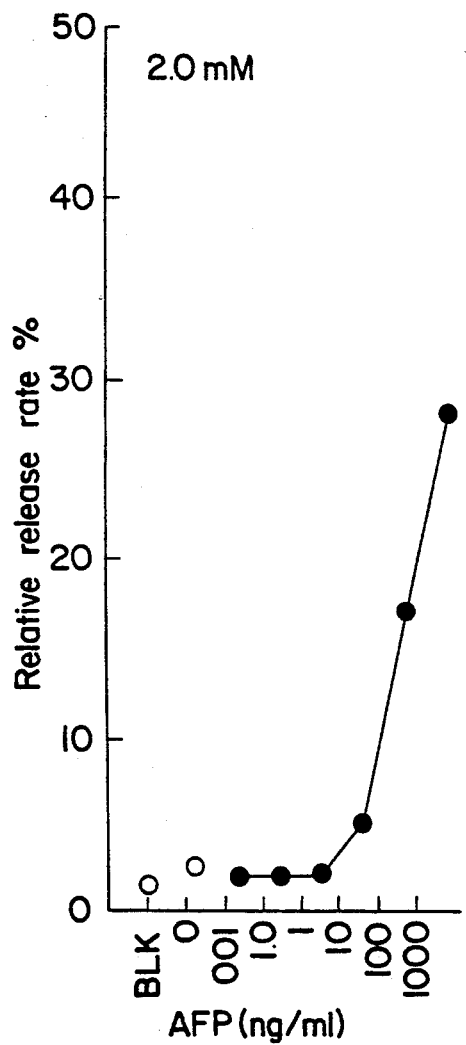
Figure 11E:
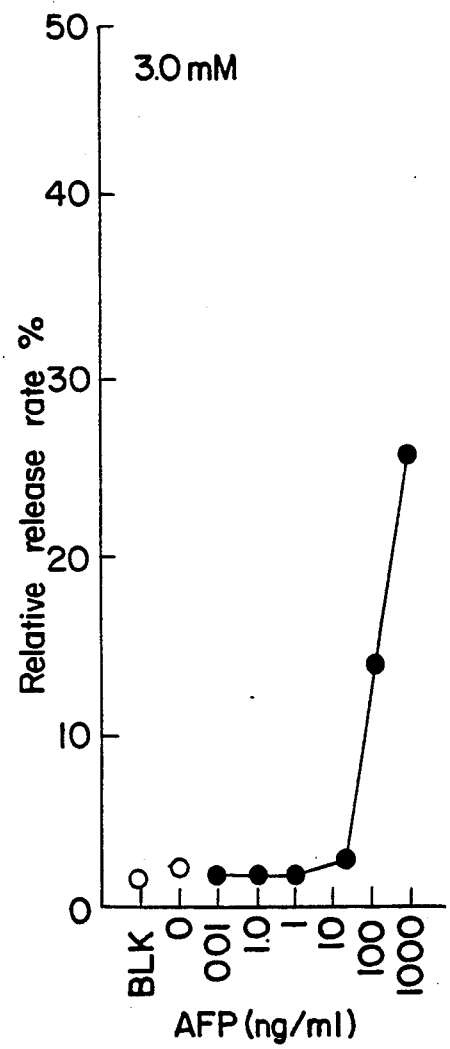

With regard to the marker (contained) material in the human IgG immobilized liposomes in Example 1, investigation was given as follows:

In the first place, glucose oxidase (a 5% solution) which was an enzyme was introduced into the liposomes. To an antibody solution which was a sample, glucose the last concentration of which was 500 μM was added, and the procedure of Example 1 was repeated. After 30 minutes' reaction at 37° C., the decrease in dissolved oxygen was measured by an oxygen electrode. FIG. 9 shows the relation between a dilution rate of the antibody and a relative release rate which was obtained by regarding, as 100%, an release rate in the case that 10% Triton X-100 was added in place of the antibody.

Figure 10:
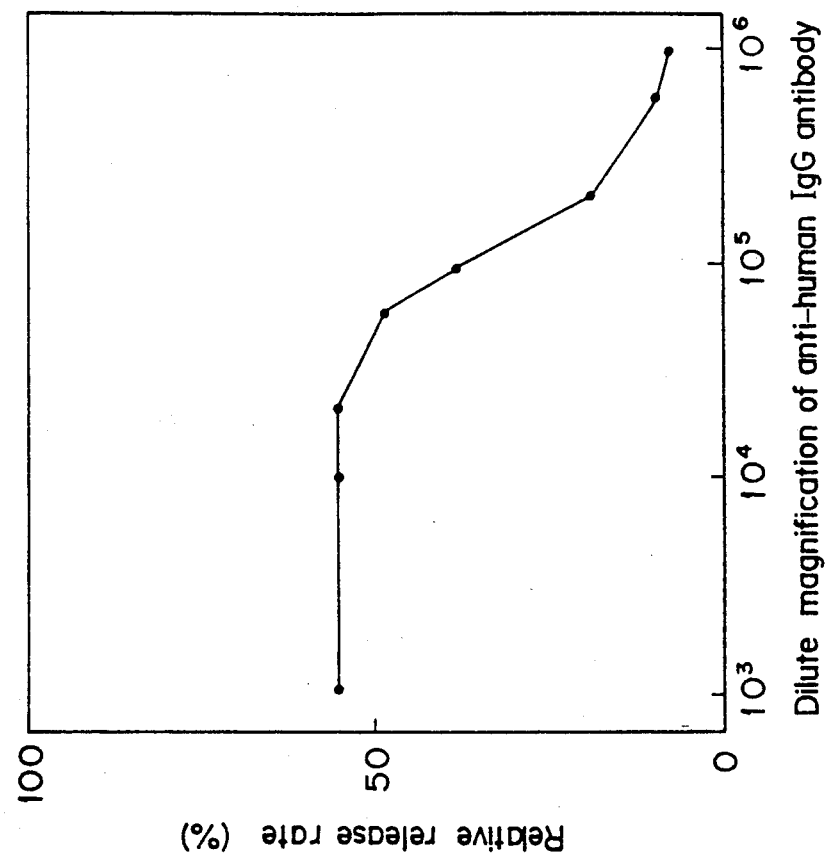
FIG. 10 is a characteristic diagram showing the correlation between a concentration of an anti-human IgG antibody and a relative release rate of a marker material in the case that the anti-human IgG antibody was determined using the human IgG bearing-liposomes which was enclosed luciferin as the marker material.

Next, a luciferin (0.1M) solution was introduced into the liposomes, and ATP having a last concentration of 1 mM and a 0.1% luciferase solution were added to an antibody solution which was a sample. After an antigen-antibody reaction, an emission volume within 30 minutes was measured. FIG. 10 shows the relation between a relative release rate and an antibody dilution rate, which relative release rate was obtained by regarding, as 100% a value obtained in the case that 10% Triton X-100 was used.

From the above-mentioned results, it was confirmed that also when enzyme or the luminescent material was introduced into the liposomes, there could be obtained determination results which were substantially similar to those of the fluorescent material.

EXAMPLE 13

Assay of human AFP

Of the reagents used in the present test example, there were used dipalmitoylphosphatidyl ethanolamine (DPPE), dipalmitoylphosphatidyl choline (DPPC), cholesterol and dithiothreitol (DTT) which were available from Sigma Inc.

Also used were N-succinimidyl-3-(2-pyridyldithio)-propionate (SPDP) and Sephadex G-25 Fine which were available from Pharmasia Fine Chemicals Inc. Other reagents were commercially available products (special grade), which were directly used without any purification. Also, ion-exchange water was used as water.

(1) Modification of anti-human AFP antibody

Diluted with HBS were 2 ml of 1 mg/ml anti-human AFP antibody, to which 10 μl of a 10 mM SPDP ethanol solution were added, and, after replaced with nitrogen, the reaction was carried out for 30 minutes at room temperature to introduce a dithiopyridyl group in the anti-human AFP antibody Next, gel filtration using a Sephadex G-25 Fine column (gel volume: about 15 ml) previously equilibrated with a 0.1M acetic acid buffer solution (containing 0.85% of NaCl; pH 4.5) was effected to remove and purify the unreacted SPDP, thus recovering only the protein fraction.

Next, about 20 mg of DTT were added to this fraction, and, after replaced with nitrogen, the reaction was carried out for 20 minutes at room temperature to effect modification by replacing the dithiopyridyl group with the SH group. Subsequently, the unreacted DTT was removed for purification by using a Sephadex G-25 Fine column equilibrated with HBS, to recover only the protein fraction.

(2) Preparation of anti-human AFP antibody immobilized liposomes

Mixed were a liposome precipitate formed by centrifuging 1 ml of the liposome suspension obtained in Example 1, and 2 ml of a 0.1 g protein/ml modified anti-human AFP antibody solution obtained in (1), and, after replaced with nitrogen, the reaction was carried out overnight under a stoppered state with slowly shaking at 20° C. Next, the mixture was washed with HBS to remove unreacted antibodies.

In the liposome reagent thus obtained, 2 ml of a gelatin Veronal buffer (pH 7.4 or less; hereinafter "GVB") and 20 μl of 10% $NaN_3$ were added. The mixture was thoroughly stirred, and, after replaced with nitrogen, stored at 4° C.

(3) Examination on blocking agent

Using the liposomes obtained in Example 1 (having been not sensitized with the antibody), examined was the effect exerted by the blocking agent on the nonspecific lysis of liposomes that is caused in the presence of a serum (final addition concentration: 1 mM).

A fresh normal human pooled serum (hereinafter "NHS") was diluted to 1/10 with $GTB^{2+}$ containing 3.2 mM for each of dithiothreitol, 2-mercaptoethanol, cysteine, glutathione, ascorbic acid, methionine and sodium glutamate, or with $GVB^{2+}$. A 25 μl portion of each diluted NHS was poured into a well of a microtiter plate (96 wells), to which 5 μl of the liposome reagent (diluted to 1/30 with $GVB^{2+}$) were added, and, after stirring, the reaction was carried out for 10 minutes at 37° C. Next, 50 ml of a complement ($5CH_{50}$) were added to carry out the reaction for 30 minutes at 37° C. Subsequently, the reaction was stopped with use of 100 μl of a 0.01M EDTA-Veronal buffer, and the quantity of released CF was measured in respect of the human AFP solutions having the respective concentration, with use of a fluorospectrophotometer MTP-32 (produced by Corona Electric Co., Ltd.) and under the conditions of an excitation wavelength of 490 nm and a fluorescence wavelength of 520 nm.

Based on this measurement, the relative fluorescence intensity was calculated according to the following equation.

$$\text{Relative fluorescence intensity} = \frac{Fe - Fo}{Fa - Fo} \times 100$$

Here, Fe: fluorescence intensity actually measured; Fo: fluorescence intensity originating from a buffer solution or sample; Fa: fluorescence intensity observed when all of the liposomes were destroyed by adding deionized water. Also, used as a standard value was fluorescence intensity of $10^{-6}$ M and $10^{-7}$ M CF solutions.

The thus obtained effect by the co-present blocking agent against the nonspecific lysis of liposomes are shown in Table 1.

TABLE 1

| Blocking agent | GVB++ | NHS | Relative fluorescence intensity |
|---|---|---|---|
| — | + | — | 8.5 |
| — | — | + | 34.8 |
| Dithiothreitol | — | + | 7.5 |
| 2-Mercaptoethanol | — | + | 7.6 |
| Cystein | — | + | 8.2 |
| Glutathione | — | + | 30.0 |
| Ascorbic acid | — | + | 34.7 |
| Methionine | — | + | 34.3 |
| Sodium glutamate | — | + | 34.3 |

Final concentration: 1 mM

The background of the liposomes was 8.5% when GVB$^{2+}$ was used as a base, and, in contrast thereto, increased to 34.8% when NHS (diluted to 1/10) was added in place of GVB$^{2+}$. This is due to the nonspecific lysis mentioned previously. The nonspecific lysis was clearly prevented when SH compounds such as dithiothreitol, 2-mercaptoethanol and cysteine were added to 1/10 NHS, and returned to the level equal to GVB$^{2+}$. Even with use of the SH compound, glutathione showed a poor effect. No substitution effect for the SH compound was observed in respect of mere reducing agents such as ascorbic acid and amino acids such as methionine and sodium glutamate.

(4) Influence of the amount for the addition of cysteine, exerted on the assay of AFP in serum Using the liposomes obtained in (2), sensitized with anti-human AFP antibodies, examined was the effect of adding cysteine to be exerted on the assay of AFP in a serum base.

NHS was diluted to 1/10 with use of GVB$^{2+}$ containing 0 to 6 mM cysteine, and AFP originating from a human placenta was added to each to give the amount of 0.1 to 1,000 mg/ml. Next, a 25 μl portion of each sample was poured into a well of a microtiter plate (96 wells), to which 5 μl of the liposome reagent (an anti-human AFP antibody sensitized product; diluted to 1/30 with GVB$^{2+}$) [25 μl each of a second antibody (rabbit anti-human AFP antiserum; A=0.1) diluted with GVB$^{2+}$ containing 1 to 3 mM cysteine and a complement (10CH$_{50}$/ml)] were added, and, after stirring, the reaction was carried out for 40 minutes at 37° C. In the last place, the reaction was stopped with use of 100 ul of a 0.01M EDTA-Veronal buffer (pH 7.4), and the fluorescence intensity of the reaction mixture was measured in the same manner as in (3).

Results obtained are shown in the drawing. As will be clear from the drawing, a remarkable nonspecific lysis is observed in the system in which no cysteine is added. In contrast thereto, however, the nonspecific lysis is clearly suppressed under the cysteine concentration of 0.7 mM or more, showing a good dose response over 1 ng/ml to 1,000 ng/ml of AFP.

(5) Measurement of human AFP concentration by use of anti-human AFP antibody immobilized liposome reagent (cysteine collection concentration: 1.5 mM)

Using the same method as in (4), measured was human AFP concentration in an NHS base to prepare a calibration curve. Next, using this calibration curve, actually measured was human AFP concentration with regard to 10 samples of patients' serums. Results obtained are shown in Table 2. In Table 2, the reference example indicates the values measured by RIA.

TABLE 2

| Sample No. | Measured AFP value (ng/ml) | |
|---|---|---|
| | Reference example | Example |
| 1 | 8 | 10 |
| 2 | 25 | 23 |
| 3 | 34 | 32 |
| 4 | 58 | 61 |
| 5 | 60 | 59 |
| 6 | 259 | 260 |
| 7 | 532 | 530 |
| 8 | 650 | 640 |
| 9 | 740 | 770 |
| 10 | 1100 | 1100 |

As will be clear from Table 2, in the immunoassay according to the present test examples, there were obtained measured values well coincident with the values measured by RIA.

EXAMPLE 14

Assay of human CEA

Using liposomes sensitized with anti-human CEA monoclonal antibodies, prepared on the basis of the methods of (1) and (2) in Example 13, human CEA concentration was measured on 10 samples of patients' serums in the same manner as in Example 13. Here, the final concentration for the addition of cysteine was set to 2 mM. Results obtained are shown in Table 3. In Table 3, the reference example also indicates the values measured by RIA.

TABLE 3

| Sample No. | Measured CEA value (ng/ml) | |
|---|---|---|
| | Reference example | Example |
| 1 | 3 | 3 |
| 2 | 4 | 4 |
| 3 | 5 | 4 |
| 4 | 7 | 7 |
| 5 | 35 | 32 |
| 6 | 58 | 59 |
| 7 | 80 | 78 |
| 8 | 96 | 97 |
| 9 | 180 | 175 |
| 10 | 360 | 380 |

As will be clear from Table 3, in the immunoassay according to the present test examples, there were obtained measured values well coincident with the values measured by RIA.

As described above in detail, according to the immunoassay of this invention, there can be exhibited the effect such that a sample such as serum containing target substances can be analyzed while suppressing the nonspecific reaction and without excessively diluting it, and the target substances can be precisely and simply determined.

We claim:

1. In an immunoassay employing an immunoassay reagent comprising liposomes made from phospholipids, glycolipids or a mixture thereof, a marker material encapsulated in said liposomes, and an antibody, antibody fragment, or an antigen, immobilized on said liposomes by a cross-linking method using a cross-linker comprising a dithiopyridyl group, wherein said immunoassay method comprises the steps of
    (a) adding a sample to said liposomes in the presence of complement, and
    (b) determining the extent to which said marker is released, the improvement wherein in step (a), said addition of sample to said liposomes is effected in the further presence of a disulfide-reducing material that cleaves the disulfide bond of said dithiopyridyl group, whereby non-specific lysis of said liposomes is prevented.

2. The immunoassay according to claim 1, wherein said liposomes further comprise cholesterol.

3. The immunoassay according to claim 1, wherein said disulfide-reducing material is 2-mercaptoethanol.

4. The immunoassay according to claim 1, wherein said disulfide-reducing material is cysteine.

* * * * *